(12) United States Patent
Lutz

(10) Patent No.: US 8,408,293 B2
(45) Date of Patent: *Apr. 2, 2013

(54) REDUCING METHANE SLACK WHEN STARTING AND STOPPING BIOGAS FERMENTERS

(75) Inventor: Peter Lutz, Munich (DE)

(73) Assignee: BEKON Energy Technologies GmbH & Co. KG, Unterfoehring (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/602,228

(22) Filed: Sep. 3, 2012

(65) Prior Publication Data

US 2012/0329120 A1   Dec. 27, 2012

Related U.S. Application Data

(63) Continuation of application No. 13/134,123, filed on May 31, 2011, now Pat. No. 8,272,436, which is a continuation of application No. PCT/EP2009/066133, filed on Dec. 1, 2009.

(30) Foreign Application Priority Data

Dec. 1, 2008 (DE) .......................... 10 2008 059 803

(51) Int. Cl.
*C12M 1/107* (2006.01)
*E21B 43/22* (2006.01)

(52) U.S. Cl. ..................................... 166/246; 435/300.1
(58) Field of Classification Search .................. 166/246; 435/300.1

See application file for complete search history.

(56) References Cited

FOREIGN PATENT DOCUMENTS

| DE | 102007024911.1 | 5/2007 |
|---|---|---|
| EP | 1997875 A1 | 5/2007 |
| WO | WO 02/06439 | 7/2000 |
| WO | WO 2010/063709 | 12/2008 |

*Primary Examiner* — Maryam Monshipouri
(74) *Attorney, Agent, or Firm* — Imperium Patent Works; Darien K. Wallace

(57) ABSTRACT

A novel method reduces methane slack when operating a biogas fermenter. When starting up a freshly charged fermenter, the methane portion of the produced biogas is initially so low and the portions of carbon dioxide and nitrogen are so high that the biogas cannot be directly used in a combined heat and power plant. Conventionally, the biogas generated during the startup phase has a small portion of methane that is discharged directly into the atmosphere or is flared off if the methane fraction is larger. The initially produced methane is consequently not used and becomes methane slack. To reduce methane slack, the biogas with the low methane fraction is fed to a gas treatment unit in which non-methane components of the gas mixture are partially separated, and the remaining gas mixture with a higher methane content is returned to the biogas fermenter until the methane fraction is sufficiently high.

5 Claims, 14 Drawing Sheets

REDUCING METHANE SLACK WHEN STARTING AND STOPPING BIOGAS FERMENTERS

CROSS REFERENCE TO RELATED APPLICATION

This application is a continuation of, and claims priority under 35 U.S.C. §120 from, nonprovisional U.S. patent application Ser. No. 13/134,123 entitled "Reducing Methane Slack When Starting and Stopping Biogas Fermenters," filed on May 31, 2011, now U.S. Pat. No. 8,272,436. Application Ser. No. 13/134,123 in turn is a continuation of, and claims priority under 35 U.S.C. §120 and §365(c) from International Application No. PCT/EP2009/066133, filed on Dec. 1, 2009, and published as WO0 2010/063709 A2 on Jun. 10, 2010, which in turn claims priority from German Application No. 102008059803.8, filed on Dec. 1, 2008, in Germany. This application claims the benefit under 35 U.S.C. §119 from German Application No. 102008059803.8. The subject matter of each of the foregoing documents is incorporated herein by reference.

TECHNICAL FIELD

The present invention relates to a method for reducing methane slack in the operation of biogas systems that include at least one biogas fermenter.

BACKGROUND

So-called "dry fermentation" allows pourable biomasses from organic wastes, agriculture and communal garden and park areas to be methanized without transforming the materials into a pumpable, liquid substrate. It is possible to ferment biomasses having a dry substance fraction of up to 50%. This dry fermentation method is disclosed, e.g., in EP 0934998.

In "dry" fermentation, the material to be fermented is not stirred into a liquid phase as is the case in, for example, the liquid fermentation of organic wastes. Instead, the fermentation substrate introduced into the fermenter is permanently kept humid by withdrawing the percolate at the bottom of the fermenter and again spraying the percolate over the biomass. In this way, optimum living conditions for the bacteria are achieved. By recirculating the percolate, it is additionally possible to regulate the temperature and to add additives for process optimization.

The publication WO 02/06439 describes a bioreactor, or fermenter, having the form of a pre-fabricated garage that is operated along the principle of dry fermentation in a so-called batch process. Following an inoculation with previously fermented material, the fermentation substrate is filled into the fermenter with the aid of wheel loaders. A fermentation vessel that has a garage-type construction is closed by a gas-tight gate. The biomass is fermented under exclusion of air, with no further blending taking place and no additional material being supplied. The percolate that trickles out of the fermentation material is withdrawn via a drainage channel, intermediately stored in a tank, and again sprayed over the fermentation substrate for humidification. The fermentation process takes place in the mesophilic temperature range at 34-37° C. The temperature is regulated by heating the floor and wall of the fermentation vessel.

The generated biogas may be utilized in a cogeneration unit (Blockheizkraftwerk or BHKW) for the generation of electricity and heat. In order to ensure a constant, sufficient supply of biogas for the cogeneration unit, several fermentation vessels are successively operated in the dry fermentation plant. At the end of the dwell time, the fermenter volume is emptied completely and then charged anew. The fermented substrate is supplied to subsequent composting, resulting in the formation of an organic fertilizer comparable to conventional composts.

Due to the batch-type operation, the single fermenters must be shut down from time to time. For example, the biogas production must be stopped, the fermented biomass must be removed from the respective fermenter, fresh biomass must be charged into the fermenter, and the biogas production is then resumed. During startup of a freshly charged fermenter, the methane content in the generated biogas initially is so low, and the proportions of carbon dioxide and nitrogen are so high, that the direct use of the biogas in the cogeneration unit is not possible. Moreover, fresh biomass cannot be added in parallel to fermenters already running in the batch operation, as the quality of the biogas generated in the freshly charged fermenter is too poor and would have the result that the quality of the total gas flow would no longer be sufficient to use in a cogeneration unit. Depending on the size of the container and the type and quality of the biomass, it takes between five and twelve hours for the biogas generated in the freshly charged fermenter to achieve a quality that would allow its use in a cogeneration unit or that would allow it to be mixed in with the biogas from fermenters already having been operated for a longer period of time. During this startup phase of a freshly charged fermenter, the generated biogas with the lower methane content is therefore discharged directly to the atmosphere or is flared off if the methane content is higher. Thus, a portion of the generated methane is not utilized and becomes "methane slack."

The patent applications DE 102007024911.1 and EP08156915.4 disclose initially connecting the common biogas line from a plurality of fermenters operating in parallel to a gas processing plant. Inside the gas processing plant, the methane content is raised by filtering out nitrogen and carbon dioxide. As the gas processing plant is positioned along the common biogas line, it is only possible to improve the gas quality of the mixed biogas in the common biogas line. But it is not possible to improve the quality of the biogas generated directly in individual fermenters. As a consequence, it is not possible to reduce the methane slack occurring particularly during the startup of freshly charged fermenters.

The publication DE10047264A1 describes a method of separating biogas in a gas treatment unit into first partial flow having a high methane content and second partial flow having a low methane content. The first partial flow having the high methane content is supplied to a gas engine as fuel, and the second partial flow having the low methane content is recirculated into the biogas generation process.

It is therefore an object of the present invention to reduce the methane slack that is discharged or burned during the startup of a fermenter.

SUMMARY

The invention relates to a method for reducing methane slack when operating biogas systems that include at least one biogas fermenter and to a biogas system for carrying out the method. When starting up a freshly charged fermenter, the methane portion in the biogas produced is initially so low and the fractions of carbon dioxide and nitrogen are so high that direct use of the biogas in a combined heat and power (CHP) plant is not possible. During this startup phase of a freshly charged fermenter, the biogas generated with the low methane fraction is therefore discharged directly into the atmosphere or is flared off if the methane fraction is higher. This results in the non-use of a portion of the methane produced, namely methane slack. In order to prevent this, the biogas with the low methane fraction produced in the startup phase is fed to a gas treatment unit in which non-methane components of the gas mixture are partially separated and the remaining gas mixture with a higher methane fraction is returned to the biogas fermenter until the methane fraction is sufficiently high.

During the startup of biogas fermenters charged with fresh biomass, the methane content in the gas mixture escaping from the biogas fermenter continues to rise over a period of several hours before it is high enough to be supplied for its intended use. Instead of flaring off the gas mixture whose methane content is too low or directly discharging the gas mixture into the environment, the gas mixture is supplied to a gas treatment unit where non-methane components of the gas mixture are partially separated out and the remaining gas mixture with the higher methane content is recirculated to the biogas fermenter until the methane content is high enough.

A method of increasing the concentration of methane in biogas includes the steps of generating biogas in a freshly charged biogas fermenter, supplying the biogas to a gas treatment unit, increasing the concentration of methane of the biogas by partially removing non-methane components from the biogas, measuring the concentration of methane in the biogas, and recirculating the biogas into the biogas fermenter so long as the concentration of methane remains lower than a predetermined upper limit. When the concentration of methane in the biogas exceeds the predetermined upper limit, the biogas is supplied to a biogas utilization unit.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Reference will now be made in detail to some embodiments of the invention, examples of which are illustrated in the accompanying drawings.

Figure 1:
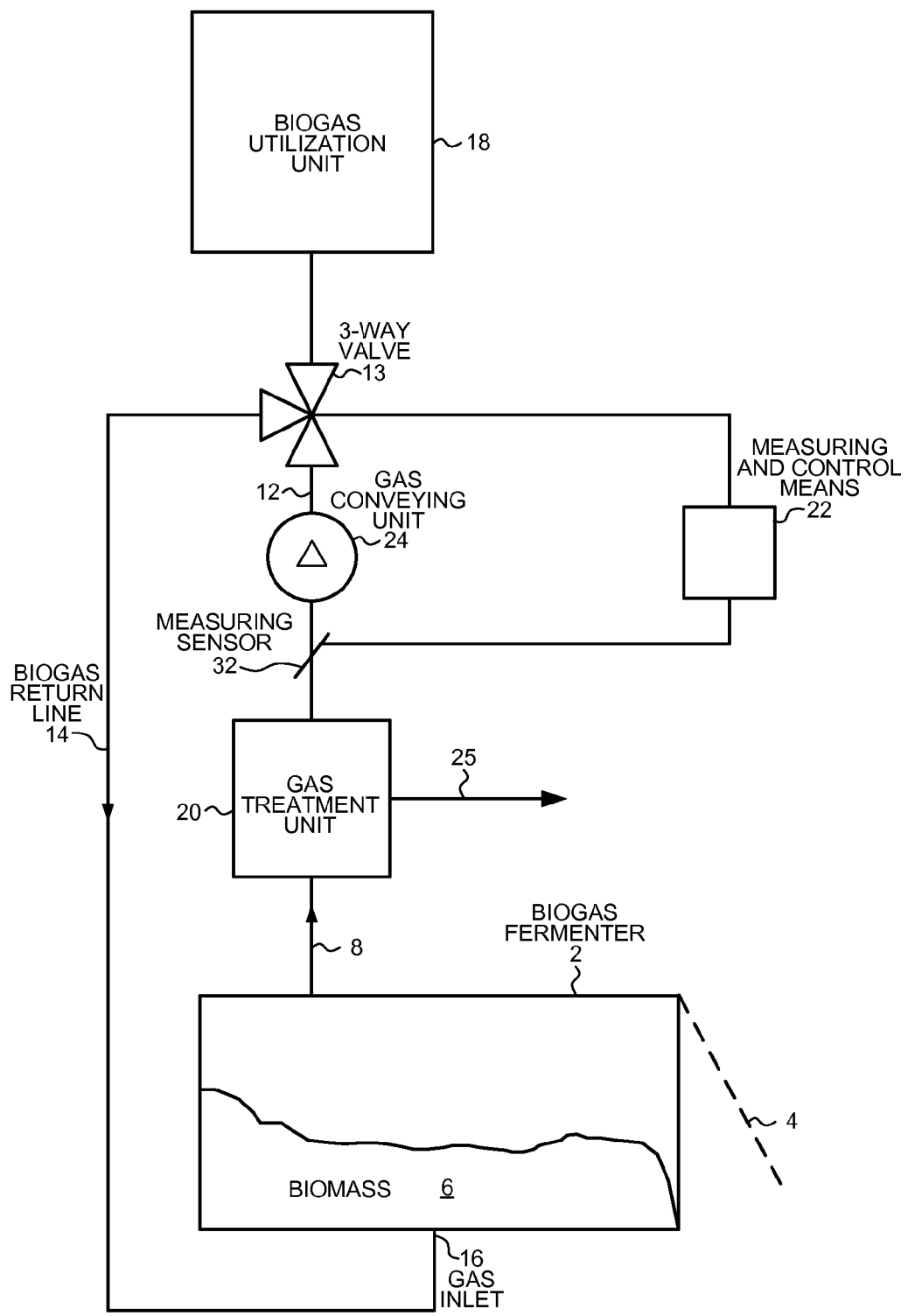
FIG. 1 is a schematic diagram of a biogas fermenter according to a first embodiment of the invention.
Figure 2:
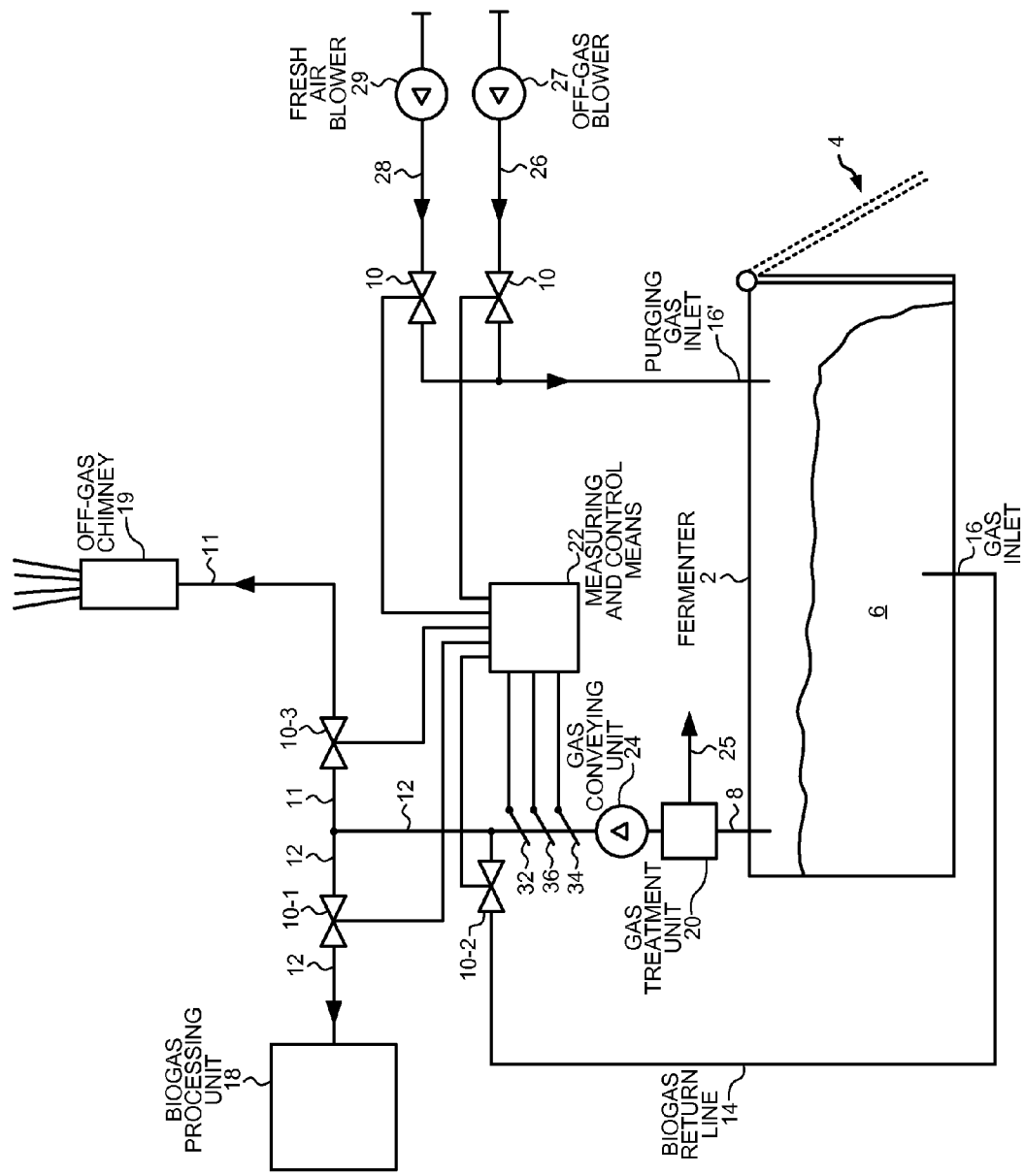
FIG. 2 is a schematic diagram of a biogas fermenter according to a second embodiment of the invention.

FIG. 1 shows a basic first embodiment of a biogas system in accordance with the present invention which comprises a single fermenter 2. The fermenter 2 is cuboid and has approximately the structure of a prefabricated garage. Biomass 6 may be charged into and removed again from the fermenter 2 with the aid of a wheel loader via a charging and emptying opening 4 extending over one of the end sides of the cuboid fermenter 2. Publication WO 02/06439 describes the detailed construction of the fermenter 2 and is incorporated herein by reference.

The fermenter 2 further includes a biogas outlet 8 that is connected to the entry of a gas treatment unit 20. The exit from the gas treatment unit 20 is connected to a biogas line 12 terminating in a 3-way valve 13. The 3-way valve 13 is adapted to be connected to a gas inlet 16 in the biogas fermenter 2 via a biogas return line 14 and to a biogas utilization or biogas processing unit 18, e.g. a cogeneration unit. The gas inlet 16 merges into the bottom area of the biogas fermenter 2. A measuring and control means 22 is connected to a measuring sensor 32 for detecting the methane concentration at the exit from the gas treatment unit 20 and to the 3-way valve 13. A gas conveying unit 24 having, for example, the form of a blower is disposed between the 3-way valve 13 and the exit from the gas treatment unit 20.

The gas treatment unit 20 acts through washing with pressurized water, filtering, or membranes to raise the quality of the generated biogas in which the non-methane components, particularly carbon dioxide, are partly separated out. The methane concentration in the gas mixture at the exit of the gas treatment unit 20 is thereby raised. The non-methane components that are separated out are discharged to the environment via an exhaust assembly 25.

During startup of the biogas fermenter 2 charged with fresh biomass, the fresh biomass 6 is sprayed with percolate such that only very little biogas is contained in the biogas fermenter 2. The gas mixture that escapes from the biogas fermenter 2 through the biogas outlet 8 is concentrated with regard to methane in the gas treatment unit 20. As long as the methane concentration measured by the measuring sensor 32 at the exit from the gas treatment unit 20 is lower than the predetermined limit ($C_{Mo}$), the 3-way valve 13 is controlled by the measuring and control means 22 such that the exit from the gas treatment unit 20 is connected to the biogas return line 14. Thus, biogas whose methane content is too low is recirculated via the biogas return line 14 and the gas inlet 16 back into the biogas fermenter 2. Only after the methane concentration in the biogas at the exit of the biogas treatment unit 20 is higher than the limit $C_{Mo}$ is the biogas supplied to the cogeneration unit 18 through the 3-way valve 13. In this way, the methane slack is reduced.

The second embodiment of the invention is now described by way of FIGS. 2-5. Analogous components as in FIG. 1 are labeled with identical reference symbols. With the exception of the 3-way valve 13, all of the components of the first embodiment are also present in the second embodiment.

In the second embodiment, the 3-way valve 13 is replaced with an arrangement of three valves 10-1, 10-2 and 10-3. Downstream from the gas conveying unit 24, a biogas/off-gas line 11 branches off from the biogas line 12. Valve 10-1 is disposed in the biogas line 12 upstream of the cogeneration unit 18. Valve 10-2 is disposed in the biogas return line 14. Valve 10-3 is disposed in the biogas/off-gas line 11. The biogas/off-gas line 11 opens into an off-gas chimney 19.

In addition to the gas inlet 16, the fermenter 2 also includes a purging gas inlet 16' that opens into the ceiling area of the biogas fermenter 2. The purging gas inlet 16' is adapted to be connected to an off-gas line 26 or to a fresh air line 28 via valves 10. An off-gas blower 27 is arranged in the off-gas line 26 such that the off-gas may be pumped into the fermenter 2. A fresh air blower 29 for sucking in fresh air from the environment is arranged in the fresh air line 28. Off-gas containing carbon dioxide is conducted as a purging gas via the off-gas line 26, and fresh air is conducted into the fermenter 2 via the fresh air line 28.

The valves 10 in off-gas line 26 and fresh air line 28 are connected to the measuring and control means 22 and are opened and closed by the latter. In addition to the measuring sensor 32 for methane concentration, the measuring and control means 22 is furthermore connected to a measuring sensor 34 for detecting the carbon dioxide concentration and to a measuring sensor 36 for detecting the gas flow rate. Both the measuring sensor 34 and the measuring sensor 36 are disposed at the exit from the gas treatment unit 20.

Figure 3:
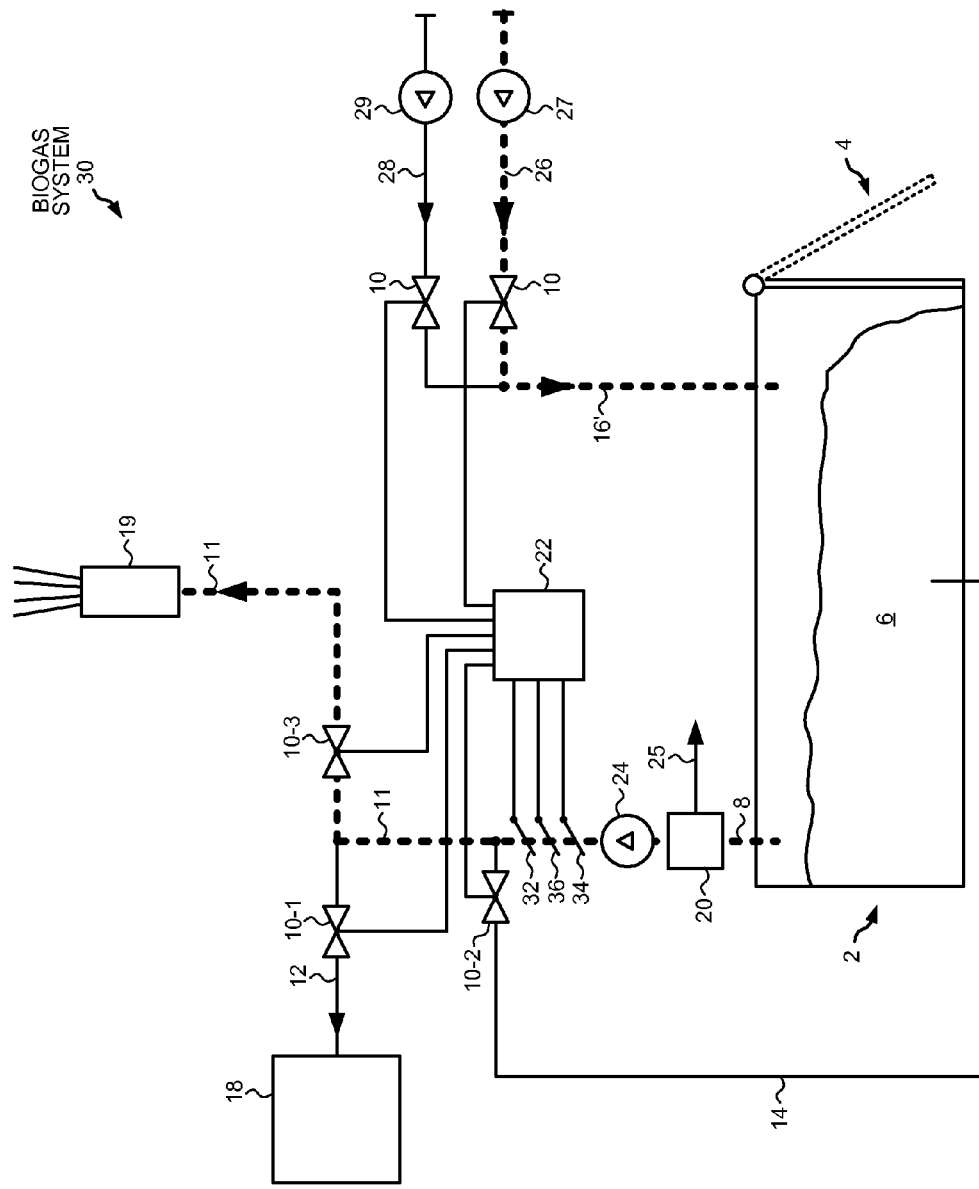
FIGS. 3-5 are diagrams showing the different phases of the startup of a biogas fermenter charged with fresh biomass.
Figure 4:
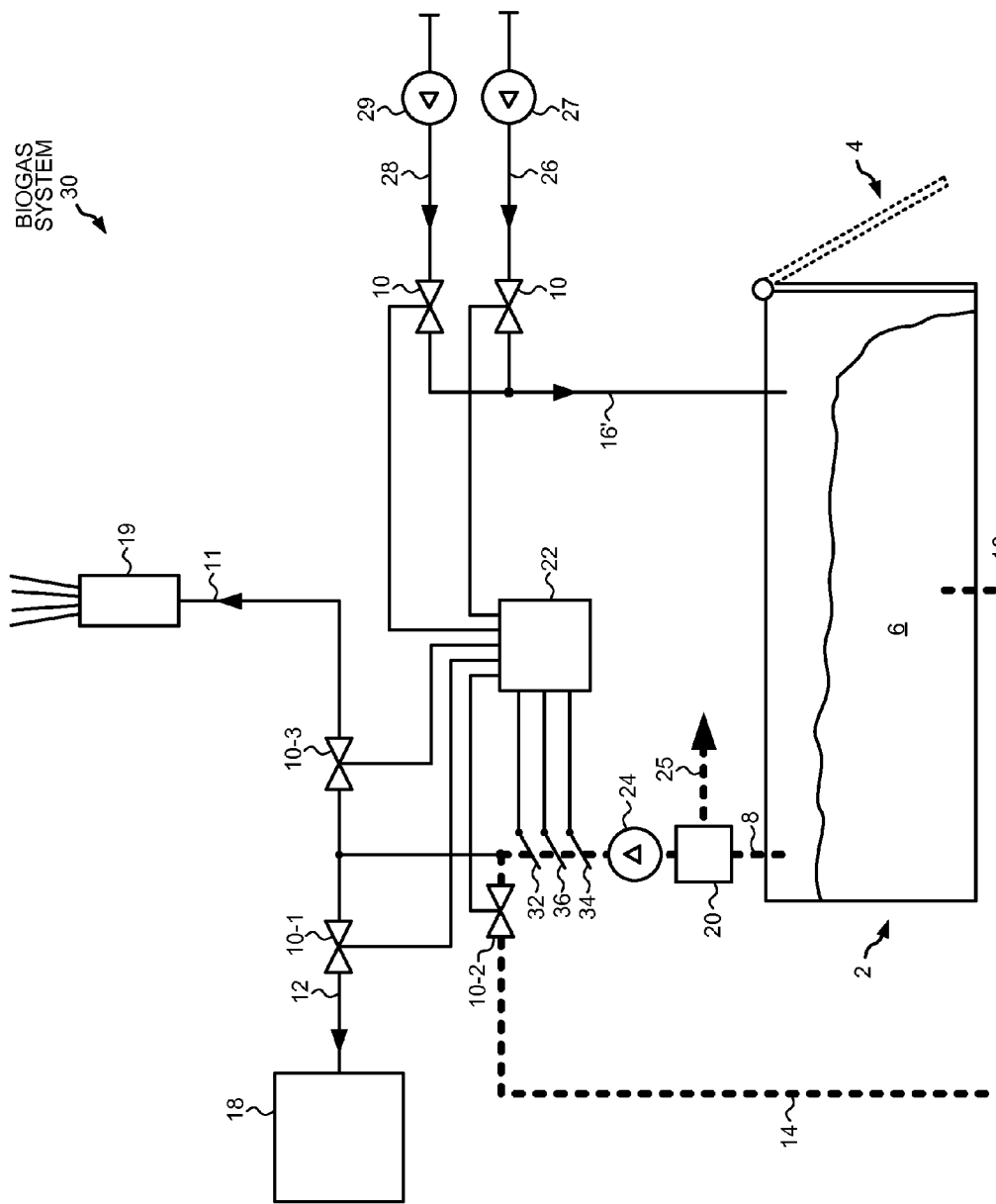
Figure 5:
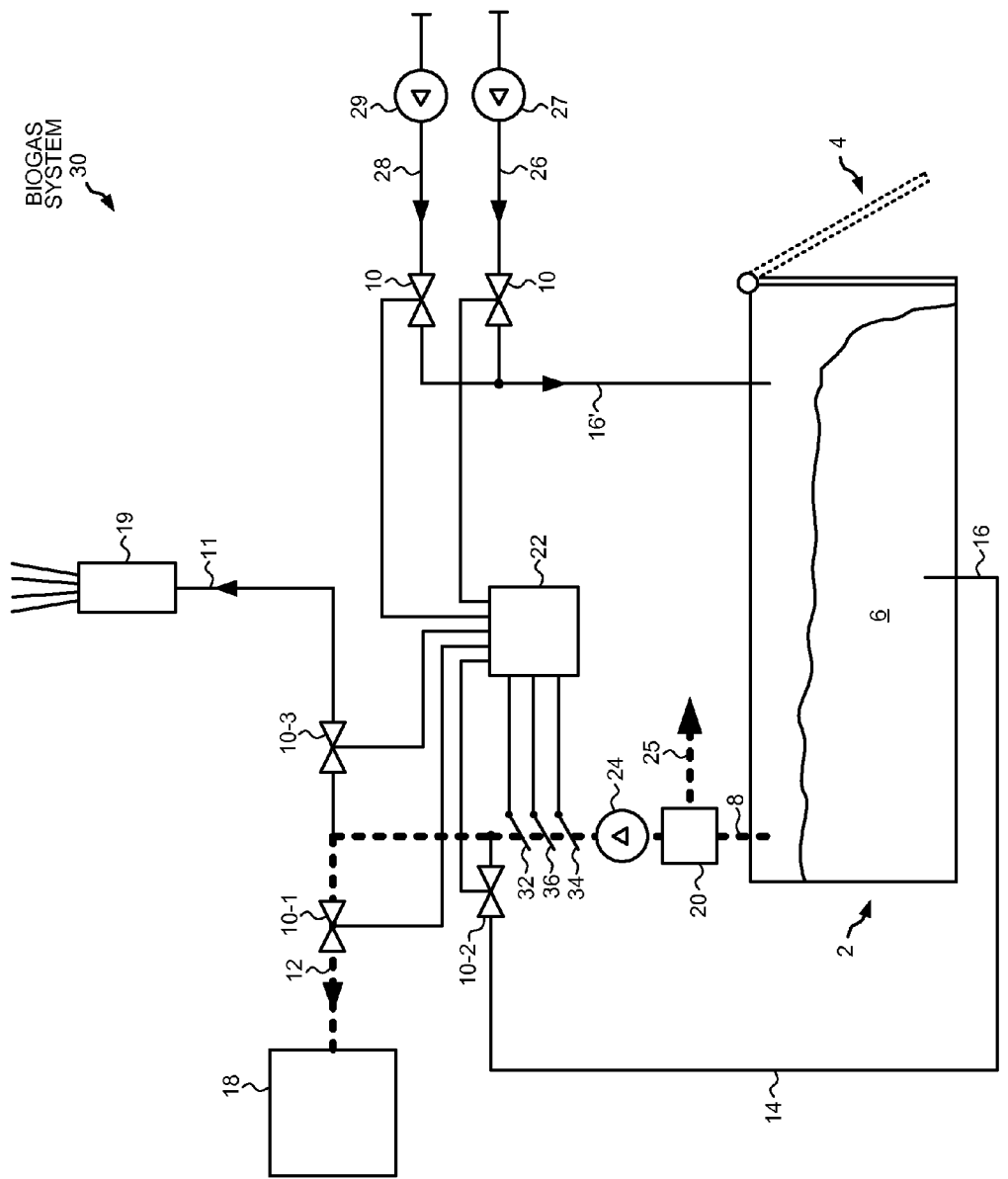

FIGS. 3-5 represent various phases of the startup of the biogas fermenter 2 charged with fresh biomass 6. Dashed lines in FIGS. 3-5 represent active lines and positions of the components of the biogas system 30.

FIG. 3 shows the first phase of the startup of the biogas fermenter 2 charged with fresh biomass 6. The charging and emptying opening 4 is closed, and the connection between biogas outlet 8 and off-gas chimney 19 via the biogas/off-gas line 11 is controlled open. In this first phase, the biogas treatment unit 20 is not active and merely passes the gas mixture. The measuring and control means 22 opens the valve 10 in the off-gas line 26 so that carbon dioxide-containing off-gas is pumped into the biogas fermenter 2. The off-gas is pumped into the fermenter 2 until the carbon dioxide concentration at the exit of the inactive gas treatment unit 20 as detected by the second measuring sensor 34 reaches or exceeds an upper limit $C_{KDo}$. In addition, the methane concentration at the exit of the inactive gas treatment unit 20 is detected by the measuring sensor 32. FIG. 4 shows the biogas system 30 once the detected methane concentration reaches or exceeds a lower limit $C_{Mu}$ and the gas treatment unit 20 is activated. When the methane concentration reaches or exceeds a lower limit $C_{Mu}$, the valve 10-3 is closed and the valve 10-2 is opened so that the gas mixture concentrated with regard to methane in the gas treatment unit 20 is recirculated through the biogas return line 14 and the gas inlet 16 into the biogas fermenter 2. The biogas recirculation is continued until the methane concentration detected by the measuring sensor 32 at the exit of the gas treatment unit 20 reaches or exceeds the upper limit $C_{Mo}$.

When the methane concentration reaches or exceeds the upper limit $C_{Mo}$, the valve 10-1 is opened and the valve 10-2 is closed so that the biogas concentrated in the gas treatment unit 20 is supplied to the cogeneration unit 18, as shown in FIG. 5. The "normal" biogas production phase has now been reached.

Shutting down the biogas fermenter 2 takes place in the manner described in patent application EP08156915.4, the subject matter of which is incorporated herein by reference.

FIGS. 6-14 show a third embodiment of the present invention in which three fermenters 2-1, 2-2 and 2-3 are utilized in parallel operation for the generation of biogas. Analogous components to those of the biogas system 30 in FIGS. 3-5 are labelled with identical reference symbols. In the biogas system 37 of FIGS. 6-14, each of the three fermenters 2-1, 2-2, 2-3 is provided with a purging gas inlet 16'-1, 16'-2 and 16'-3 as well as a gas inlet 16-1, 16-2 and 16-3 that are each adapted to be cut off by a valve 10. The three purging gas inlets 16'-$i$ are combined into a common purging gas inlet line 42. An off-gas line 26 and a fresh air line 28, each of which is adapted to be cut off by a valve 10, open into the common purging gas inlet line 42. In another embodiment, the purging gas inlets 16-$i$ and 16'-$i$ are combined into one common purging gas inlet line (not shown).

Each of the three fermenters 2-1, 2-2, 2-3 is provided with a biogas outlet 8-1, 8-2 and 8-3, each of which is adapted to be cut off by a valve 10. Downstream from the valves 10, the single biogas outlets 3-$i$ are combined into a common biogas line 12 opening into a cogeneration unit 18 as a biogas consumer. Between the valves 10 and the biogas fermenters 2-$i$ respective partial biogas/off-gas lines 40-1, 40-2 or 40-3 branch off from the biogas outlets 8-$i$. Each of the biogas/off-gas lines 40-1, 40-2 or 40-3 are adapted to be cut off by a valve 10 and are combined into a common biogas/off-gas line 40 downstream from the valves 10. The biogas/off-gas line 40 is connected to the inlet of a gas treatment unit 20 whose outlet is connected to a gas conveying unit 24. The gas conveying unit 24 merges into a 4-way valve 31 controlled through the intermediary of a control unit 22. The remaining valves 10 are equally operated by the control unit 22, even though this is not explicitly represented in FIGS. 6-14. Downstream from the 4-way valve 31 the biogas/off-gas line 40 leads to an off-gas chimney 19. From the 4-way valve 31, a biogas return line 14 branches off and leads back into the gas inlets 16-$i$ of the individual biogas fermenters 2-$i$. From the 4-way valve 31, a biogas supply line 38 branches off and merges into the common biogas line 12.

An exhaust line 44 from the cogeneration unit 18 merges into a second off-gas chimney 46. The off-gas line 26 is connected to the exhaust line 44 via a 3-way valve 48 such that the carbon dioxide-containing off-gas occurring in the cogeneration unit 18 is used to purge a fermenter 2-$i$ intended to be shut down. The flow rate of the off-gas conveyed for purging a fermenter 2-$i$ through the off-gas line 26 and the quantity of the off-gas discharged to the environment via the second off-gas chimney 46 are regulated using 3-way valve 48.

A first measuring sensor 32 for detecting the methane concentration is disposed in the common biogas line 12. A second measuring sensor 34 for detecting the carbon dioxide concentration, a third measuring sensor 36 for detecting the flow rate, and a fourth measuring sensor 50 for detecting the methane concentration are disposed in the common biogas/off-gas line 40 downstream of the gas treatment unit 20 and downstream of the blower 24. The four measuring sensors 32, 34, 36 and 50 are connected to a control unit 22. The control lines to the measuring sensors are not shown in FIGS. 6-14. The valve 10 in the off-gas line 26 can be optionally omitted, as its function may also be assumed by the 3-way valve 48.

In FIGS. 6-14, various phases for shutting down and restarting the second fermenter 2-2 are represented. The biogas production of the first and third fermenters 2-1 and 2-3 goes on continuously during shutdown and restart of the second fermenter 2-2.

Figure 6:
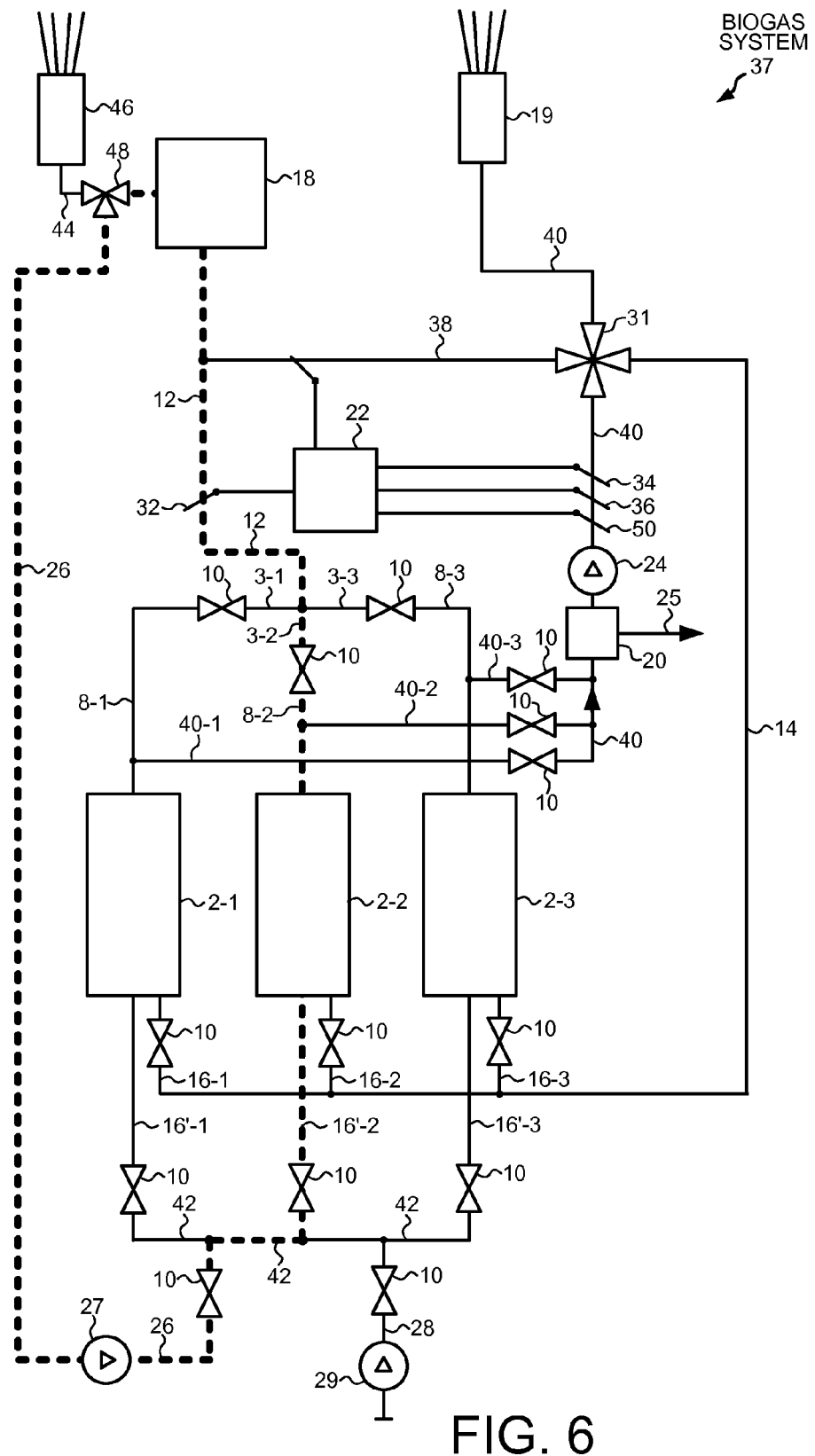
FIGS. 6-14 are schematic representations of a third embodiment of the invention that includes a plurality of biogas fermenters operated in parallel during various operating states.

FIG. 6 shows the first phase of shutting down the second fermenter 2-2. Carbon dioxide-containing off-gas is pumped from the cogeneration unit 18 via the 3-way valve 48 and the off-gas line 26, through the off-gas blower 27 and the second purging gas inlet 16'-2 into the fermenter 2-2. The second biogas outlet 8-2 continues to be connected to the common biogas line 12, so that the biogas/off-gas mixture continues to be supplied to the cogeneration unit 18.

Figure 7:
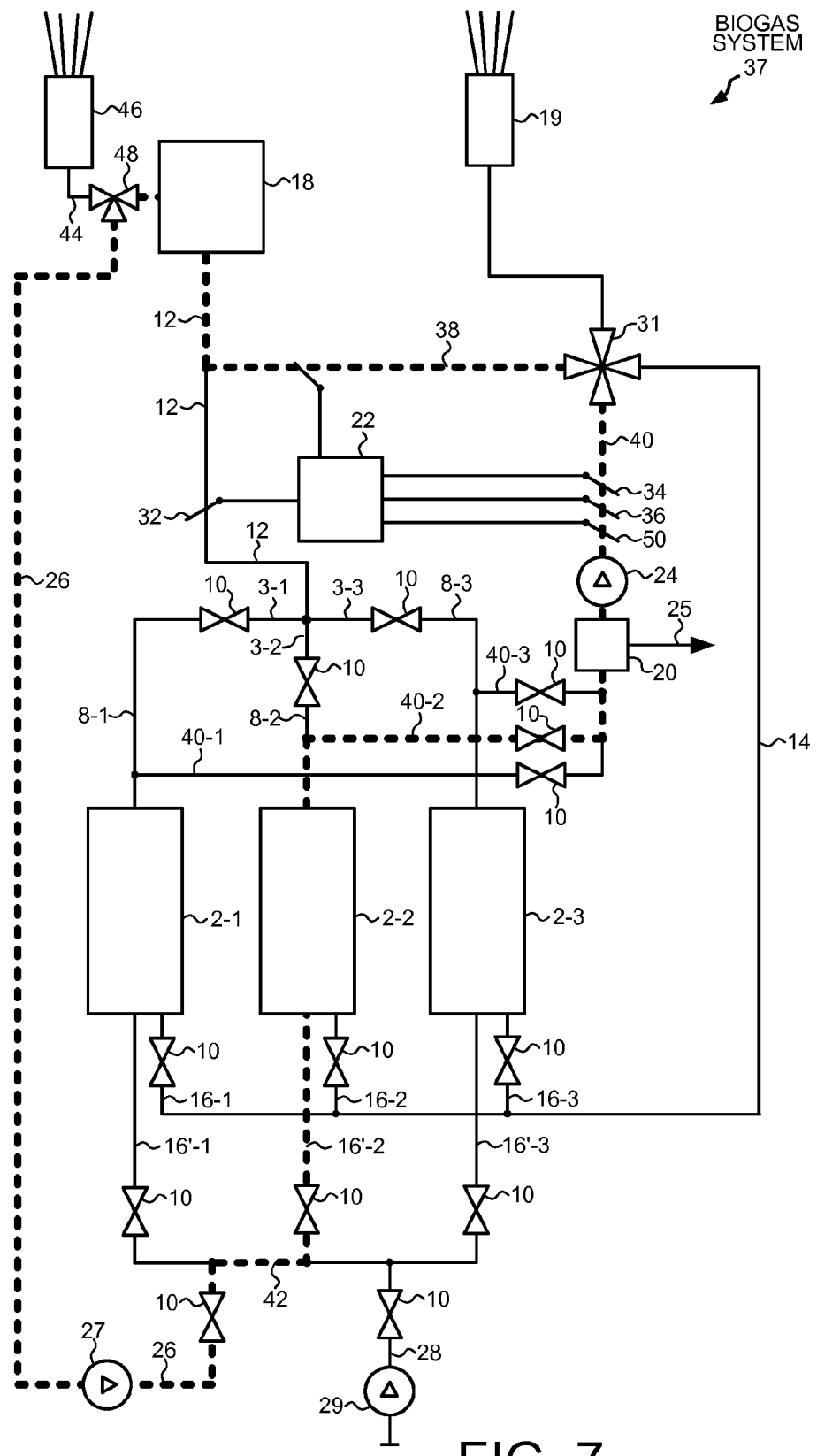

FIG. 7 shows the second phase of shutting down the second fermenter 2-2. Only after the methane concentration detected by the first measuring sensor 32 in the common biogas line 12 has dropped below an upper limit $C_{Mo}$ is the valve 10 in the second biogas outlet 8-2 closed by the control unit 22, and the valve 10 in the second partial biogas/off-gas line 40-2 is opened, as shown in FIG. 7. So long as the methane concentration detected by the fourth measuring sensor 50 at the exit from the gas treatment unit 20 is higher than the upper limit $C_{Mo}$, the biogas/off-gas mixture is concentrated with regard to methane in the gas treatment unit 20 and supplied to the common biogas line 12 via the 4-way valve 31 and the biogas supply line 38. In this second phase of the shutdown of the fermenter 2-2, in the gas treatment unit 20 the carbon dioxide-containing off-gas is partly removed from the biogas/off-gas mixture in the partial biogas/off-gas line 40-2, and the remaining biogas/off-gas mixture presenting a sufficient methane concentration continues to be supplied to the cogeneration unit 18 together with the biogas from the biogas fermenters 2-1 and 2-3.

Figure 8:
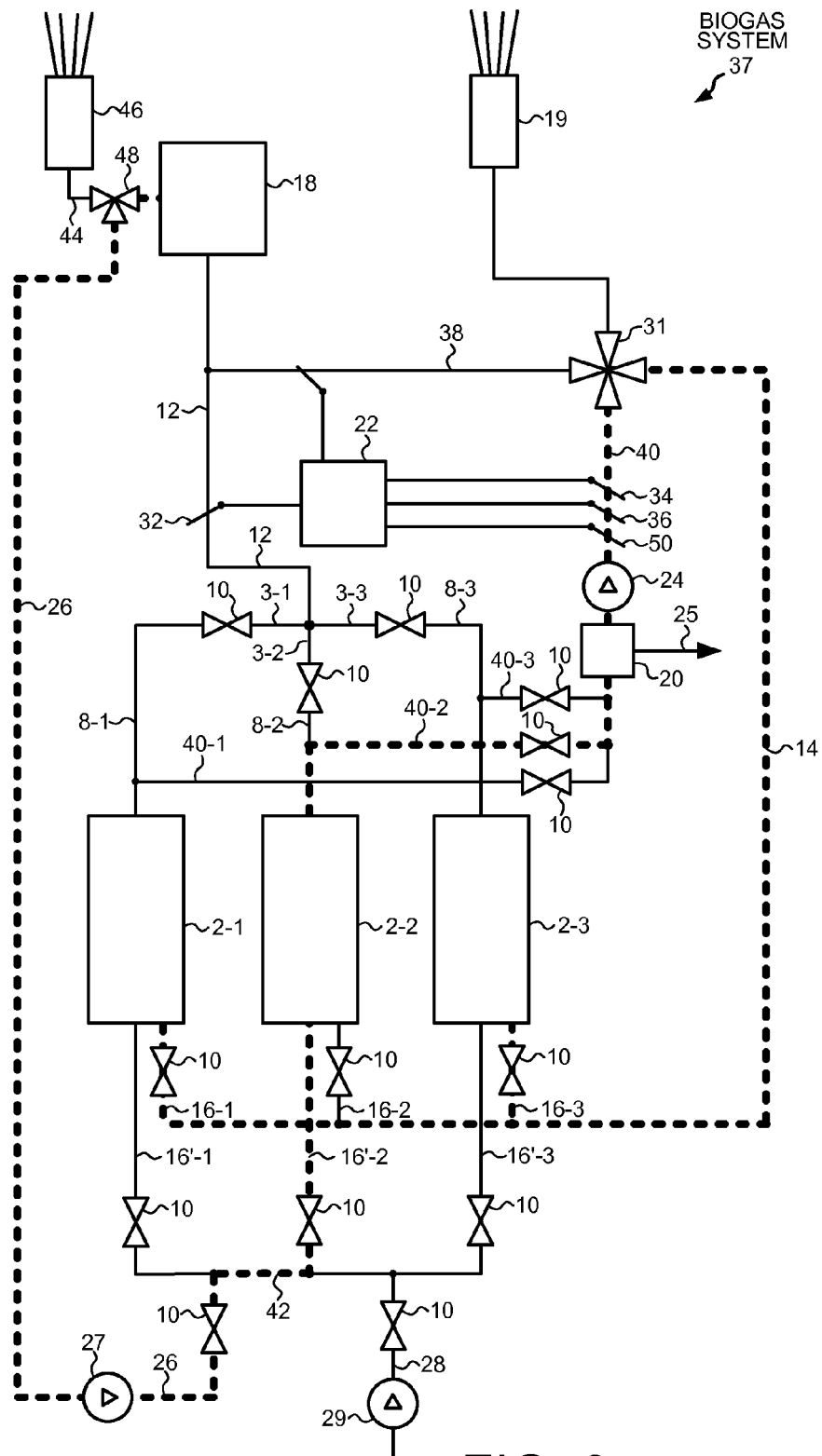

FIG. 8 shows the third phase of shutting down the second fermenter 2-2. Once the methane concentration detected by the fourth measuring sensor 50 in the common biogas/off-gas line 40 downstream from the gas treatment unit 20 has dropped below the upper limit $C_{Mo}$, the 4-way valve 31 connects the common biogas/off-gas line 40 to the biogas return line 14, and the biogas/off-gas mixture is supplied into the two other biogas fermenters 2-1 and 2-3 through the gas inlets 16-1 and 16-3. This third phase of the shutdown is continued until the methane concentration detected by the first measuring sensor 32 drops below the upper limit $C_{Mo}$, or the methane concentration detected by the fourth measuring sensor 50 in the common biogas/off-gas line 40 drops below the lower limit $C_{Mu}$, depending on which occurs first.

Figure 9:
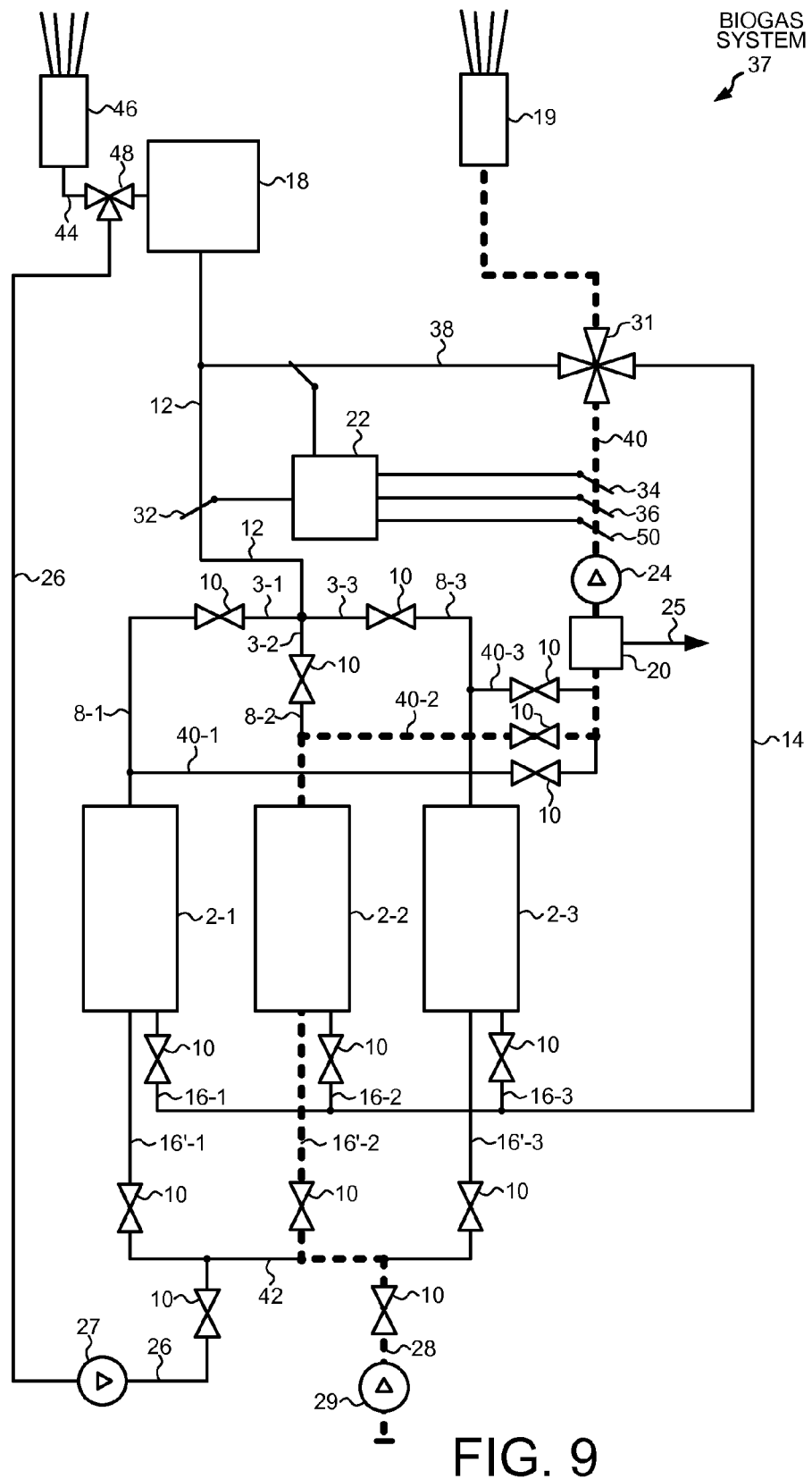

FIG. 9 shows the fourth phase of shutting down the second fermenter 2-2. Once either the methane concentration detected by the first measuring sensor 32 has dropped below the upper limit $C_{Mo}$ or the methane concentration detected by the fourth measuring sensor 50 at the exit from the gas treatment unit 20 in the common biogas/off-gas line 40 has dropped below the lower limit $C_{Mu}$, whichever occurs first, the valve 10 in the off-gas line 26 is closed and the valve 10 in the fresh air line 29 is opened by control unit 22. The control unit 22 connects the common biogas/off-gas line 40 to the first off-gas chimney 19 with the aid of the 4-way valve 31, and the gas treatment unit 20 is deactivated. The biogas/off gas/air mixture having a very low methane content is directly discharged to the environment via the first off-gas chimney 19. This fourth phase of the shutdown is performed until the carbon dioxide concentration detected by the second measuring sensor 34 in the common biogas line 40 has dropped below a lower limit $C_{KDu}$.

Figure 10:
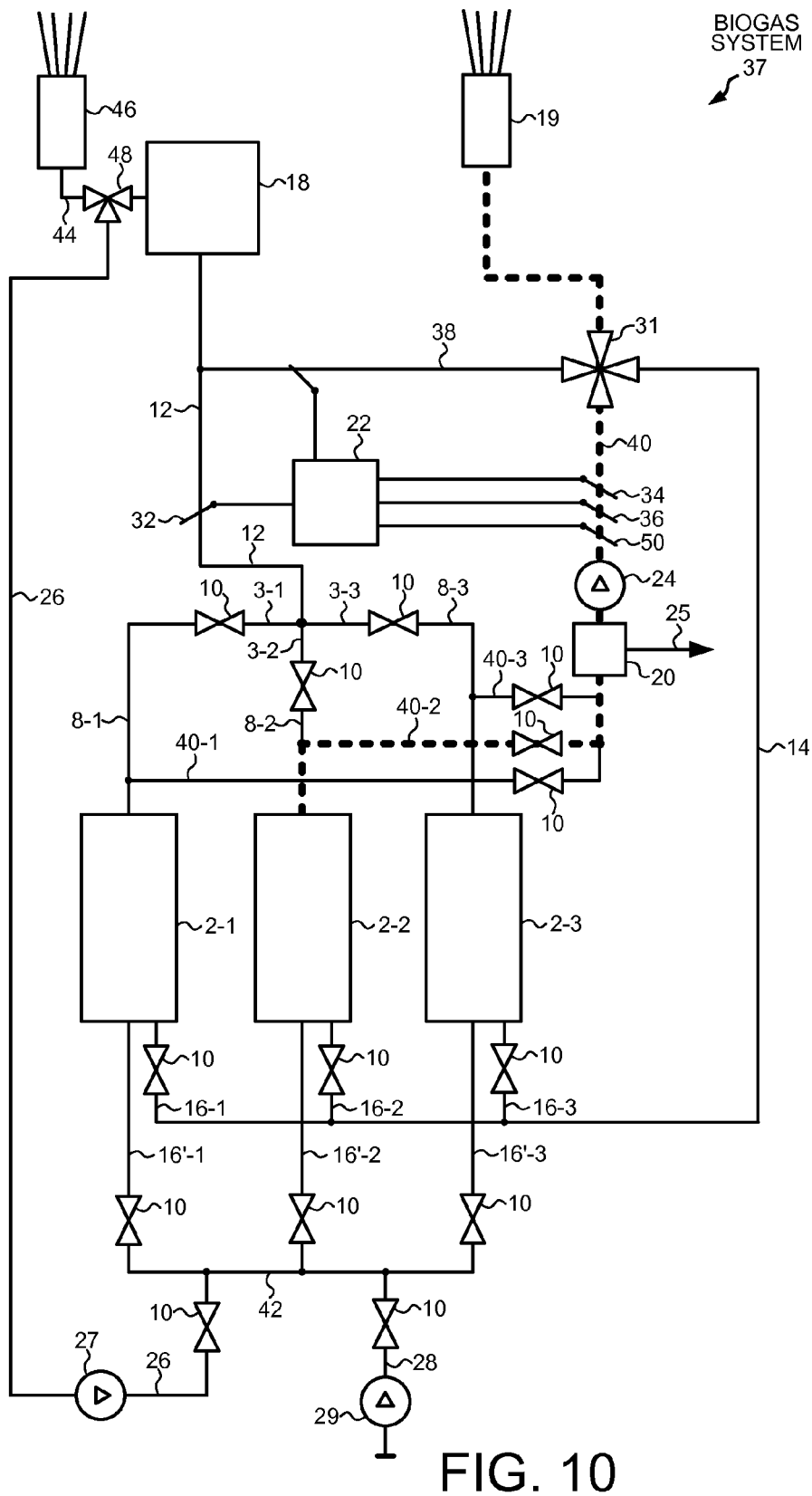

FIG. 10 shows the fifth phase of shutting down or emptying the second fermenter 2-2. Once the carbon dioxide concentration detected by the second measuring sensor 34 in the common biogas/off-gas line 40 has dropped below the lower limit $C_{KDu}$, the valve 10 in the fresh air line 28 is closed by the control unit 22 and the fresh air blower 29 is deactivated. The charging and emptying opening (shown in FIGS. 3-5 but not in FIGS. 6-14) is opened. Concurrently, fresh air is sucked in by the blower 24 in the common biogas/off-gas line 40 via the open charging and emptying opening and discharged to the environment through the off-gas chimney 19. This prevents residual biogas still contained in the fermented biomass from presenting a risk to the operating personnel during emptying. It also serves to evacuate exhaust gases of a wheel loader used for charging and emptying.

Figure 11:
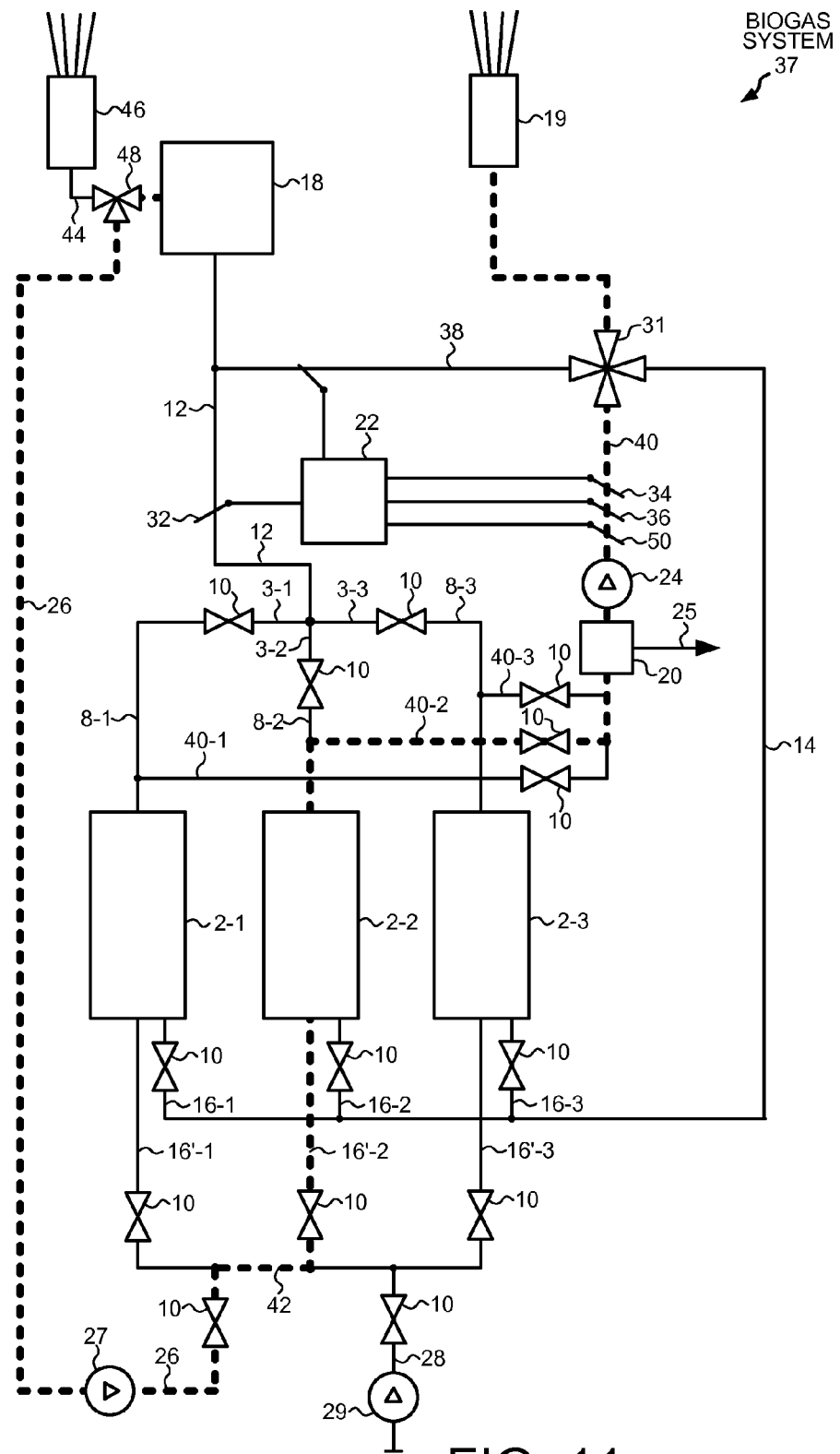

FIG. 11 shows the first phase of starting up the second fermenter 2-2. After the fermenter 2-2 has again been charged with fresh biomass, the charging and emptying opening is closed. The connection between second biogas outlet 8-2 and off-gas chimney 19 through the second partial biogas/off-gas line 40-2 and the common biogas/off-gas line 40 is maintained open. And the control unit 22 opens the valve 10 in the off-gas line 26 and turns off the 3-way valve 48 in the exhaust line 44 of the cogeneration unit 18 so that carbon dioxide-containing off-gas is pumped into the fermenter 2-2. The gas treatment unit 20 is not active. This first phase of restarting the biogas fermenter 2 is continued until the methane concentration in the common biogas/off-gas line 40 detected by the fourth measuring sensor 50 reaches the lower limit $C_{Mu}$.

Figure 12:
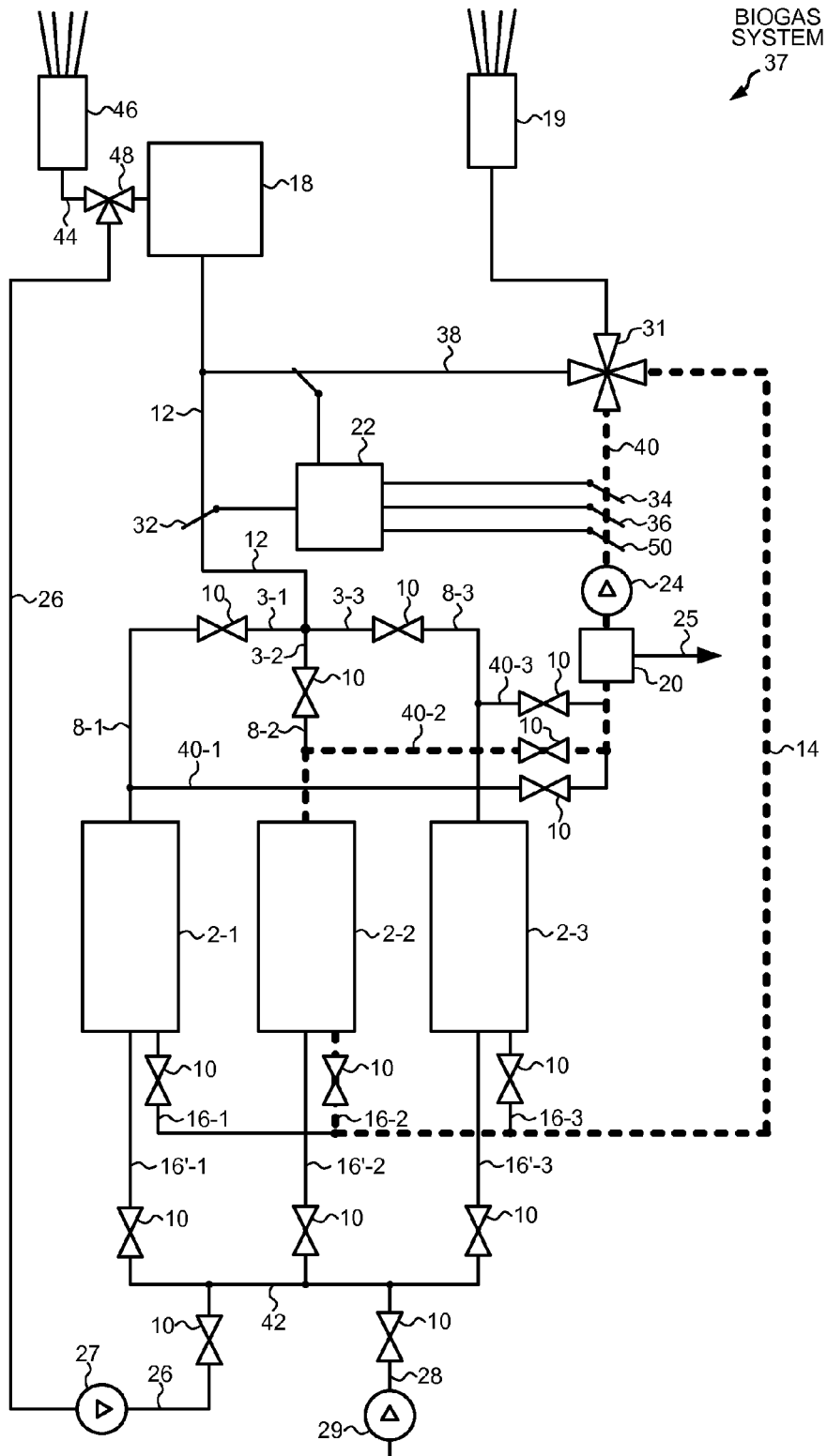

FIG. 12 shows the second phase of starting up the second fermenter 2-2. Once the lower limit $C_{Mu}$ of methane concentration has been reached, the supply of off-gas via the off-gas line 26 is stopped, and the gas treatment unit 20 is activated. The control unit 22 causes the common biogas/off-gas line 40 to be connected to the biogas return line 14 through the 4-way valve 31. The biogas/off-gas mixture concentrated in the gas treatment unit 20 is recirculated via the biogas return line 14 into the biogas fermenter 2 that is intended to be started up. This second phase of the startup is maintained until the methane concentration detected by the fourth measuring sensor 50 at the exit from the gas treatment unit 20 reaches the upper limit $C_{Mo}$.

Figure 13:
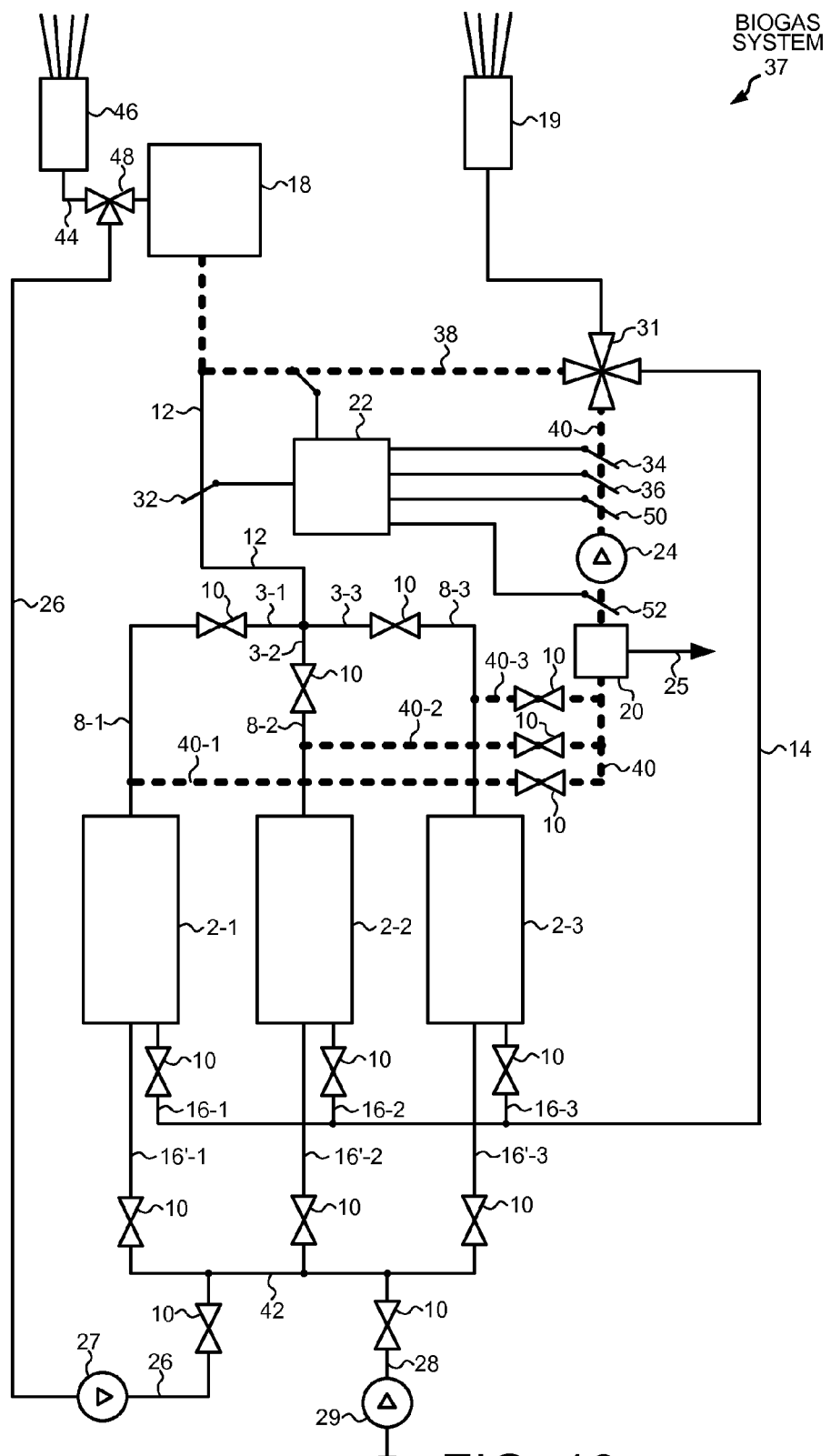

FIG. 13 shows the third phase of starting up the second fermenter 2-2. Once the methane concentration detected by the fourth measuring sensor 50 reaches the upper limit $C_{Mo}$, the common biogas/off-gas line 40 is connected to the biogas supply line 38 by means of the control unit 22 and the 4-way valve 31. In addition, the partial biogas/off-gas lines 40-1 and 40-3 are furthermore connected to the common biogas/off-gas line 40 so that the biogas from all biogas fermenters 2-$i$ is now concentrated in the gas treatment unit 20.

Figure 14:
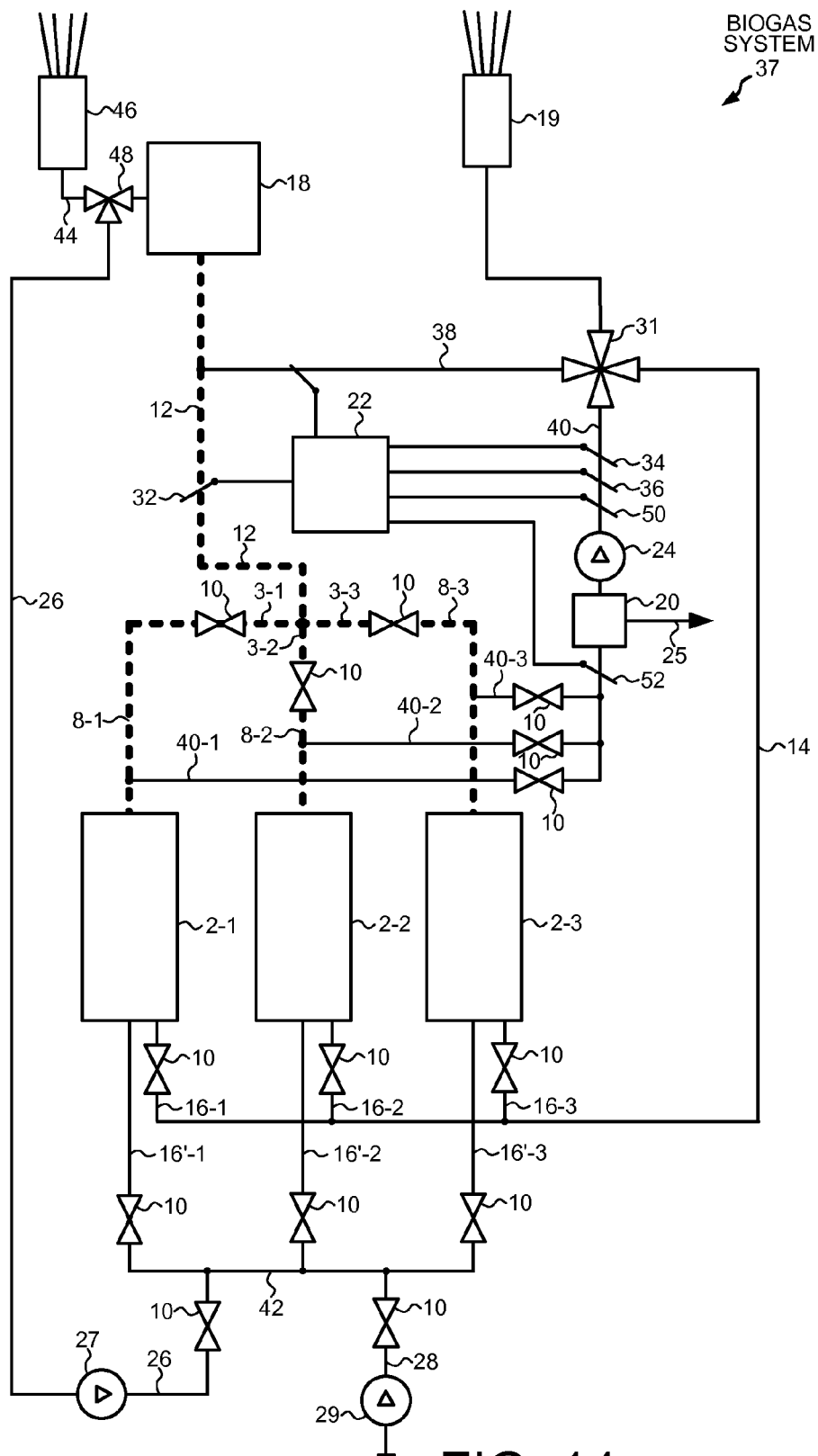

FIG. 14 illustrates the normal operation of the three biogas fermenters 2-1, 2-2 and 2-3. If the difference between the methane concentration downstream as measured by the fourth measuring sensor 50 and the methane concentration upstream from the gas treatment unit 20 as measured by the fifth measuring sensor 52 drops below the predetermined limit $C_{M3}$, the normal operation of the biogas system has been achieved. The biogas generated in all biogas fermenters 2-$i$ is then supplied directly to the common biogas line 12 via the biogas outlets 8-$i$, and the gas treatment unit 20 is deactivated.

Instead of the normal operation as shown in FIG. 14, the switching configuration as shown in FIG. 13 may equally be maintained as the normal operation. As a further alternative, it is possible in the normal operation of FIG. 13 to provide another gas treatment unit (not shown) that would then be disposed immediately upstream of the cogeneration unit 18. By means of pressurized water washing, filtering or membranes, the gas treatment units increase the methane content and decrease the carbon dioxide content and thereby increase the quality of the generated biogas to the qualitative level of natural gas.

Exemplary numerical values for the various limits are indicated below:

Methane Concentration:

| | |
|---|---|
| upper limit $C_{Mo}$ | 30% to 50% |
| lower limit $C_{Mu}$ | 0% to 3% |
| limit $C_{M3}$ | 0% to 1% |

Carbon Dioxide Concentration:

| | |
|---|---|
| lower limit $C_{KDu}$ | 0.5% to 2% |
| upper limit $C_{KDo}$ | 5% to 15% |

Depending on the capacity of the fermenters and the amount of available off-gas, the off-gas flow rate in the off-gas line 26 is between 150 and 1000 m³/h. The fresh air flow rate in the fresh air line 28 is between 1000 and 5000 m³/h.

| List of Reference Symbols: | |
|---|---|
| 2 | fermenter |
| 4 | charging and emptying opening |
| 6 | biomass |
| 8 | biogas outlet |
| 10 | valve |
| 11 | biogas/off-gas line |
| 12 | biogas line |
| 13 | 3-way valve |
| 14 | biogas return line |
| 16 | gas inlet |
| 16' | purging gas inlet |
| 18 | biogas utilization or biogas processing unit |
| 19 | off-gas chimney |
| 20 | gas treatment unit |
| 22 | measuring and control means |
| 24 | gas conveying unit |
| 25 | exhaust assembly |
| 26 | off-gas line |
| 27 | off-gas blower |
| 28 | fresh air line |
| 29 | fresh air blower |
| 30 | biomass system |
| 31 | 4-way valve |
| 32 | measuring sensor for methane concentration |
| 34 | measuring sensor for carbon dioxide concentration |
| 36 | measuring sensor for flow rate |
| 38 | biogas supply line |
| 40 | common biogas/off-gas line |
| 40-1 | first partial biogas/off-gas line |
| 40-2 | second partial biogas/off-gas line |
| 40-3 | third partial biogas/off-gas line |
| 42 | common purging gas inlet |
| 44 | exhaust line |
| 46 | second off-gas chimney |
| 48 | 3-way valve |
| 50 | fourth measuring sensor (methane concentration) |
| 52 | fifth measuring sensor (methane concentration) |

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method comprising:
   generating biogas in a freshly charged biogas fermenter, wherein the biogas has a concentration of methane;
   supplying the biogas to a gas treatment unit;
   increasing the concentration of methane of the biogas by partially removing non-methane components from the biogas;
   measuring the concentration of methane in the biogas; and
   recirculating the biogas into the biogas fermenter so long as the concentration of methane remains lower than a predetermined upper limit.

2. The method of claim 1, further comprising:
   supplying the biogas to a biogas utilization unit when the concentration of methane exceeds the predetermined upper limit.

3. The method of claim 1, further comprising:
   connecting a biogas outlet of the biogas fermenter to an off-gas chimney after the concentration of methane falls below a predetermined lower limit.

4. The method of claim 1, wherein the predetermined upper limit of the concentration of methane falls within the range of 30% to 50% of the biogas by volume.

5. The method of claim 1, further comprising:
   generating biogas in a second biogas fermenter at the same time as the generating the biogas in the freshly charged biogas fermenter.

* * * * *